United States Patent [19]

Hall et al.

[11] 4,279,930
[45] Jul. 21, 1981

[54] PROCESS FOR TREATING INFLAMMATION

[75] Inventors: Charles M. Hall; Eldridge M. Glenn, both of Kalamazoo, Mich.

[73] Assignee: The Upjohn Company, Kalamazoo, Mich.

[21] Appl. No.: 75,822

[22] Filed: Sep. 14, 1979

Related U.S. Application Data

[63] Continuation of Ser. No. 949,457, Oct. 10, 1978, abandoned.

[51] Int. Cl.³ .................... C07C 49/248; A01N 35/00
[52] U.S. Cl. ............................ 424/331; 424/324; 424/330; 424/311; 568/334; 560/255; 564/305
[58] Field of Search ............... 568/331; 260/558 R, 260/559 R, 570 AB; 560/250, 251, 252, 255; 424/331, 311, 308, 324, 330

[56] References Cited

U.S. PATENT DOCUMENTS

| | | | |
|---|---|---|---|
| 2,647,148 | 7/1953 | Martin et al. | 424/331 |
| 2,769,817 | 11/1956 | Martin et al. | 424/179 |
| 3,137,621 | 6/1964 | Lafon | 424/331 |
| 3,686,319 | 8/1972 | Lafon | 424/331 |
| 3,817,752 | 6/1974 | Laudon et al. | 568/331 |
| 3,928,421 | 12/1975 | Kyogoku et al. | 424/331 |

OTHER PUBLICATIONS

Sallai et al., Chem. Abst., vol. 85, #57378p, (1976).
Winget, Biochem., vol. 8(5), pp. 2067–2074, (1969).
Diedrich, J. Med. Pharm. Chem., vol. 5, pp. 1054–1062, (1962).

*Primary Examiner*—Joseph E. Evans
*Assistant Examiner*—James H. Reamer
*Attorney, Agent, or Firm*—John J. Killinger

[57] ABSTRACT

A process for treating inflammation locally or topically by administering a compound of the formula:

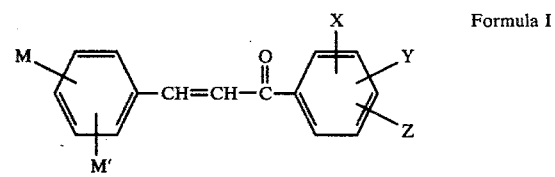

Formula I wherein M and M' are hydrogen, hydroxy, halogen, lower alkyl of from 1 to 3 carbon atoms, lower alkoxy of from 1 to 3 carbon atoms; $NH_2$, RNH, $R'_2N$ where R is lower alkyl of from 1 to 3 carbon atoms or lower acyl of from 1 to 3 carbon atoms and R' is lower alkyl of from 1 to 3 carbon atoms; X, Y and Z are hydrogen, hydroxy, halogen, lower alkoxy of from 1 to 3 carbon atoms or lower acyloxy of from 1 to 6 carbon atoms, in association with appropriate pharmaceutical carriers.

10 Claims, No Drawings

PROCESS FOR TREATING INFLAMMATION

This is a continuation, of application Ser. No. 949,457, filed Oct. 10, 1978 now abandoned.

BRIEF DESCRIPTION OF THE INVENTION

A process for the localized treatment of inflammation by topical application or local injection of compounds of the formula I to humans and animals having inflammation.

DETAILED DESCRIPTION OF THE INVENTION

A process for treating inflammation locally or topically by administering a compound of the formula:

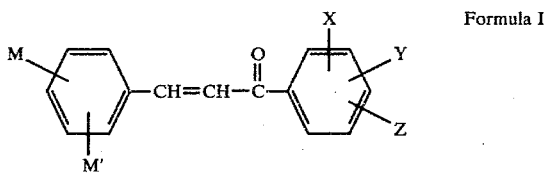

Formula I wherein M and M' are hydrogen, hydroxy, halogen, lower alkyl of from 1 to 3 carbon atoms, lower alkoxy of from 1 to 3 carbon atoms; $NH_2$, RNH, $R_2'N$ where R is lower alkyl of from 1 to 3 carbon atoms or lower acyl of from 1 to 3 carbon atoms and R' is lower alkyl of from 1 to 3 carbon atoms; X, Y and Z are hydrogen, hydroxy, halogen, lower alkoxy of from 1 to 3 carbon atoms or lower acyloxy of from 1 to 6 carbon atoms, in association with a pharmaceutical carrier.

The compounds of the formula I are known in the art, except for the compound of Example 1.

The compositions can be applied topically or by injection subcutaneously intra-dermally or intra-articularly.

The compositions are useful in the topical treatment of inflammation, for example, inflammation associated with chronic dermatitis, psoriasis, contact dermatitis, atopic and seborrheic dermatitis, and acne. The injectable compositions can also be used in treatment of rheumatoid arthritis by intra-articular injection.

The term "topical" as employed herein relates to the use of the active ingredient of the formula I incorporated in a suitable pharmaceutical carrier, and applied at the site of the inflammation for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleoginous, absorption, water-soluble and emulsion-type bases, e.g., petrolatum, lanolin, polyethylene glycols, as well as mixtures thereof. It has been found that topical application with occlusion of an area larger than the medicated area produces improved results relative to non-occluded topical application and is, therefore, the preferred method of topical treatment with the compositions of this invention.

The percentage by weight of the active ingredient herein utilizes ranges from about 0.1% to about 50% of the pharmaceutical preparation, preferably from about 0.5% to about 10%, and in these preparations the aforesaid pharmaceutical carrier for topical application constitutes a major amount of the said preparation, applied 1-4 times daily.

Injection "intradermally" refers to positioning the composition in the high dermis by needle injection, or by high pressure air injection.

Injection "intra-articularly" refers to positioning the composition into the joint at the site of the inflammation.

For parenteral administration, fluid unit dosage forms are prepared utilizing the active ingredient and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by crystallization under sterile conditions before suspending in the sterile vehicle. Advantageously, a surfactant or wetting agent is included in the composition to facilitate uniform distribution.

The percentage by w/v of the active ingredient for the injectable compositions ranges from about 0.1% to about 5% and preferably from about 0.5 to 2%, injected 1-4 times daily.

The compositions of this invention may be employed in conjunction with glucocorticoids. The expression "glucocorticoids" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate or prednisone for oral application or triamcinolone for topical therapy. The glucocorticoids should be employed in minor amounts or "permissive dosage." The expression "permissive dosage" for glucocorticoids refers to a quantity which minimally supplements the natural output of adrenal cortical glucocorticoids in a normal person and which dosage administered, alone, has no perceptible effect on proliferative skin diseases.

The following examples describe the manner and process of making and using the invention and set forth the best mode contemplated by the inventor of carrying out the invention but are not to be construed as limiting.

EXAMPLE 1

1-(2,6-dihydroxyphenyl)-3-(4-hydroxyphenyl)-prop-2-en-1-one

To a solution of 7.6 grams (0.05 mole) of 2',6'-dihydroxyacetophenone and 6.1 gram (0.05 mole) p-hydroxybenzaldehyde in ethanol was added 100 ml. of 60% aqueous sodium hydroxide. The mixture was stirred at room temperature for 18 hours and then acidified with 6 N hydrochloric acid. The resulting orange solid was collected by filtration and washed with water. The solid was chromatographed on silica gel (200 g., 2.25 l., 20% acetone-Skellysolve "B") and 150 ml. fractions taken. Fractions 6-12 were combined and crystallized from methanol-methylene chloride giving fine orange needles, 28 g., m.p. 190°-192° C., resolidified and melted 210°-212° C., 22% yield).

Analysis: Calc'd. for $C_{15}H_{12}O_4$: C, 70.30; H, 4.72. Found: C, 70.37; H, 4.86.

EXAMPLE 2

1-(2,6-dihydroxyphenyl)-3-(4-hydroxyphenyl)-prop-2-en-1-one—0.9 gm.
Cetyl alcohol—5.4 gm.
Sodium lauryl sulfate—1.35 gm.
White petrolatum—27.0 gm.
Propylene glycol—9.0 gm.
Distilled water q.s.—9.0 gm.

The oil phase is prepared by melting the petrolatum, cetyl and stearyl alcohols together. The remaining ingredients are dispersed in the water and added to the oil phase to form a cream.

The cream is useful in the treatment of inflammation by rubbing on the inflamed skin two or three times a day.

EXAMPLE 3

The following topical compositions are useful in treating psoriasis.

1-(2,6-dihydroxyphenyl)-3-(4-hydroxyphenyl)-prop-2-en-1-one—0.1 gm.
Spermaceti—27 gm.
Beeswax—27 gm.
Carbapol 934 q.s.—100 gm.

CREAM 1-(2,6-dihydroxyphenyl)-3-(4-hydroxyphenyl)-prop-2-en-1-one—1 gm.
Polyethylene glycol 400—37.5 gm.
1,2,6-hexanetriol—20 gm.
Polyethylene glycol 4000 q.s.—100 gm.

CREAM 1-(2,6-dihydroxyphenyl)-3-(4-hydroxyphenyl)-prop-2-en-1-one—5 gm.
Polyethylene glycol 400—37 gm.
Polyethylene glycol 400 monostearate—26 gm.
Polyethylene glycol 4000 q.s.—100 gm.

CREAM 1-(2,6-dihydroxyphenyl)-3-(4-hydroxyphenyl)-prop-2-en-1-one—5 gm.
Polyethylene glycol 400—47.5 gm.
Cetyl alcohol—5 gm.
Polyethylene glycol 4000 q.s.—100 gm.

OINTMENT 1-(2,6-dihydroxyphenyl)-3-(4-hydroxyphenyl)-prop-2-en-1-one—10 gm.
Anhydrous lanolin—20 gm.
Mineral oil—25 gm.
White petrolatum q.s.—100 gm.

The above ointments and creams are useful in the treatment of inflammation by application to the affected skin areas two to three times a day.

EXAMPLE 4

One thousand grams of topical cream is prepared from the following types and amounts of ingredients:

1-(2,6-dihydroxyphenyl)-3-(4-hydroxyphenyl)-prop-2-en-1-one—100 gm.
Polysorbate 80—50 gm.
Tegacid regular*—150 gm.
Spermaceti—100 gm.
Propylene glycol—50 gm.
Methylparaben—1 gm.
Deionized water q.s.—1000 gm.

*Self-emulsifying glyceryl monostearate from Goldschmidt Chemical Corporation, New York, N.Y.

The Tegacid and spermaceti are melted together at a temperature of 70°-80° C. The methylparaben is dissolved in about 500 gm. of water and the propylene glycol, polysorbate 80, and 1-(2,6-dihydroxyphenyl)-3-(4-hydroxyphenyl)-prop-2-en-1-one are added in turn, maintaining a temperature of 75°-80° C. The methylparaben mixture is added slowly to the Tegacid and spermaceti melt, with constant stirring. The addition is continued for at least 30 minutes with additional stirring until the temperature has dropped to 40°-45° C. Finally, sufficient water is added to bring the final weight to 1000 gm. and the preparation stirred to maintain homogeneity until cooled and congealed.

The composition is applied to human skin three times a day to treat inflammation.

EXAMPLE 5 Parenteral Composition

A sterile aqueous composition for injection containing in 1 cc. 50 mg. of 1-(2,6-dihydroxyphenyl)-3-(4-hydroxyphenyl)-prop-2-en-1-one is prepared from the following types and amounts of materials:

1-(2,6-dihydroxyphenyl)-3-(4-hydroxyphenyl)-prop-2-en-1-one—50 gm.
Lidocaine hydrochloride—4 gm.
Methylparaben—2.5 gm.
Propylparaben—0.17 gm.
Water for injection q.s.—1000 cc.

The ingredients are dispersed in the water under sterile conditions. The sterile composition is filled into 2 cc. vials and the vials sealed.

EXAMPLE 6 Parenteral Composition

A sterile aqueous composition for injection, containing in 1 cc. 1 mg. of 1-(2,6-dihydroxyphenyl)-3-(4-hydroxyphenyl)-prop-2-en-1-one is prepared from the following types and amounts of ingredients:

1-(2,6-dihydroxyphenyl)-3-(4-hydroxyphenyl)-prop-2-en-1-one—1 gm.
Sodium chloride q.s.
Water for injection q.s.—1000 gm.

Under sterile conditions the 1-(2,6-dihydroxyphenyl)-3-(4-hydroxyphenyl)-prop-2-en-1-one is added to the water and sufficient sodium chloride added to form an isotonic solution. The sterile composition in the amount of 2 cc. is aseptically filled into sterile vials and sealed.

The composition is injected in 0.5 cc. quantities intradermally in the area of inflammation.

EXAMPLE 7 Soluble Topical Compositions 1-(2,6-dihydroxyphenyl)-3-(4-hydroxyphenyl)-prop-2-en-1-one—2.5 gm.
Ethanol 95% v/v—97.5 ml.

The active ingredient is dissolved in the alcohol and applied topically for the treatment of psoriatic lesions.

EXAMPLE 8 Soluble Topical Compositions 1-(2,6-dihydroxyphenyl)-3-(4-hydroxyphenyl)-prop-2-en-1-one—1.0 gm.
Methanol—99.0 ml.

The active ingredient is dissolved in the alcohol and applied topically for the treatment of psoriatic lesions.

EXAMPLE 9 Soluble Topical Compositions 1-(2,6-dihydroxyphenyl)-3-(4-hydroxyphenyl)-prop-2-en-1-one—5.0 gm.
Isopropyl alcohol—95.0 ml.

The active ingredient is dissolved in the alcohol and applied topically for the treatment of psoriatic lesions.

EXAMPLE 10

Following the procedure of the preceding Examples 2 to 9, inclusive, substituting an equal amount each of
3-(4-methoxyphenyl)-1-(2,4,6-trihydroxyphenyl)-prop-2-en-1-one,
3-[4-(dimethylamino)phenyl]-1-(4-hydroxyphenyl)-prop-2-en-1-one,
3-(4-chlorophenyl)-1-(4-hydroxyphenyl)-prop-2-en-1-one,
3-(3-ethoxy-4-hydroxyphenyl)-1-(4-hydroxyphenyl)-prop-2-en-1-one,
3-(3-fluorophenyl)-1-(4-hydroxyphenyl)-prop-2-en-1-one,
1-(4-hydroxyphenyl)-3-(4-hydroxyphenyl)-prop-2-en-1-one,
1-(4-methoxyphenyl)-3-(3-methoxyphenyl)-prop-2-en-1-one,
3-(2-fluorophenyl)-1-(4-hydroxyphenyl)-prop-2-en-1-one, and
3-(4-hydroxyphenyl)-1-(4-methoxyphenyl)-prop-2-en-1-one for the 1-(2,6-dihydroxyphenyl)-3-(4-hydroxyphenyl)-prop-2-en-1-one compositions are prepared which are useful for the treatment of inflammation.

EXAMPLE 11

The compositions prepared in the preceding Examples 2 through 10, inclusive, can similarly be administered for treatment of psoriasis, eczema, contact dermatitis, occupational dermatitis, exfoliative dermatitis, urticaria, acne vulgaris and rosacea, pemphigus and pemphigoid acne, erythema multiforme, drug eruptions, and related proliferative diseases in humans and mastitis in bovines.

We claim:

1. A process for treating inflammation comprising the administration of an anti-inflammatory amount of a compound of the formula:

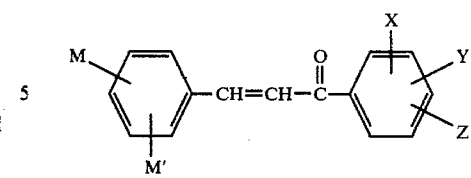

Formula I wherein M and M' are hydrogen, hydroxy, halogen, lower alkyl of from 1 to 3 carbon atoms, lower alkoxy of from 1 to 3 carbon atoms; X, Y and Z are hydrogen, hydroxy, halogen, lower alkoxy of from 1 to 3 carbon atoms or lower acyloxy of from 1 to 6 carbon atoms, in association with appropriate pharmaceutical carriers.

2. The process of claim 1 wherein M' is hydrogen.

3. The process of claim 1 where the compound is 1-(3-fluorophenyl)-3-(4-hydroxyphenyl)-prop-1-en-3-one.

4. The process of claim 1 where the compound is 1-(4-hydroxyphenyl)-3-(4-hydroxyphenyl)-prop-1-en-2-one.

5. The process of claim 1 where the compound is 1-(2,6-dihydroxyphenyl)-3-(4-hydroxyphenyl)-prop-2-en-1-one.

6. A pharmaceutical composition for treatment of inflammation comprising from about 0.1% to about 50% a compound of the formula:

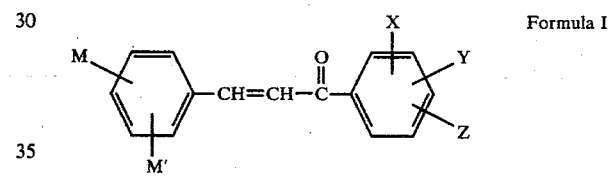

Formula I wherein M and M' are hydrogen, hydroxy, halogen, lower alkyl of from 1 to 3 carbon atoms, lower alkoxy of from 1 to 3 carbon atoms; X, Y and Z are hydrogen, hydroxy, halogen, lower alkoxy of from 1 to 3 carbon atoms or lower acyloxy of from 1 to 6 carbon atoms, in association with appropriate pharmaceutical carriers.

7. The composition of claim 6 wherein M' is hydrogen.

8. The composition of claim 6 wherein the compound is 1-(3-fluorophenyl)-3-(4-hydroxyphenyl)-prop-1-en-2-one.

9. The composition of claim 6 wherein the compound is 1-(4-hydroxyphenyl)-3-(4-hydroxyphenyl)-prop-1-en-3-one.

10. The composition of claim 6 wherein the compound is 1-(2,6-dihydroxyphenyl)-3-(4-hydroxyphenyl)-prop-3-en-1-one.

* * * * *